United States Patent
Bufe et al.

(10) Patent No.: US 9,950,017 B2
(45) Date of Patent: Apr. 24, 2018

(54) PHARMACEUTICAL COMPOSITION FOR PROTECTION FROM ALLERGIES AND INFLAMMATORY DISORDERS

(75) Inventors: Albrecht Bufe, Hamburg (DE); Otto Holst, Bad Oldesloe (DE); Harald Renz, Marburg (DE); Erika Von Mutius, Stamberg (DE); Johann Bauer, Ismaning (DE); Nicole Blumer, Edertal-Bergheim (DE); Jennifer Debarry, Hannover (DE); Markus Ege, Munich (DE); Susanne Friedrich, Dortmund (DE); Holger Garn, Marburg (DE); Soren Gatermann, Bochum (DE); Anna Hanuszkiewicz, Siemianowice Slaskie (PL); Holger Heine, Sulfeld (DE); Michael Wegmann, Colbe (DE)

(73) Assignees: FORSCHUNGSZENTRUM BORSTEL, Borstel (DE); RUHR-UNIVERSITÄT BOCHUM, Bochum (DE)

( * ) Notice: Subject to any disclaimer, the term of this patent is extended or adjusted under 35 U.S.C. 154(b) by 1927 days.

(21) Appl. No.: 12/041,553

(22) Filed: Mar. 3, 2008

(65) Prior Publication Data
US 2008/0305089 A1 Dec. 11, 2008

(30) Foreign Application Priority Data
Mar. 2, 2007 (EP) .................................. 07 004 329

(51) Int. Cl.
A61K 35/74 (2015.01)
A61K 35/744 (2015.01)

(52) U.S. Cl.
CPC ............ *A61K 35/74* (2013.01); *A61K 35/744* (2013.01)

(58) Field of Classification Search
None
See application file for complete search history.

(56) References Cited

U.S. PATENT DOCUMENTS

2008/0206284 A1   8/2008   Williams et al.

FOREIGN PATENT DOCUMENTS

| DE | 10007771 A | 8/2001 |
|---|---|---|
| DE | 202 02 562 U1 | 6/2002 |
| DE | 10101793 A | 8/2002 |
| EP | 0 178 443 A2 | 4/1986 |
| EP | 0 904 784 A1 | 3/1999 |
| EP | 1538198 A2 | 6/2005 |
| EP | 1637147 A1 | 3/2006 |
| EP | 1964570 A1 | 9/2008 |
| JP | 57009722 A2 | 1/1982 |
| JP | 10007577 A2 | 1/1998 |
| JP | 2997774 B2 | 1/2000 |
| KR | 10-2001-0106068 | 11/2001 |
| KR | 10-2004-0044300 | 5/2004 |
| WO | WO 95/31984 A | 11/1995 |
| WO | WO 96/00579 | 1/1996 |
| WO | WO 00/16786 A | 3/2000 |
| WO | WO 01/49319 A1 | 7/2001 |
| WO | WO 2005/03230 A1 | 4/2005 |
| WO | WO 2006/025068 A | 3/2006 |

OTHER PUBLICATIONS

Franks et al., Appl Environ Microbiol. Sep. 1998; 64(9): 3336-3345.*
Repa et al., Vaccine vol. 22 (2003) pp. 87-95.*
DeBarry et al. (2007). (J. Allergy Clin. Immunol. vol. 119, No. 6, pp. 1514-1521).*
Zechini et al. Diagnostic Microbiology and Infectious Disease 56 (2006) 325-328.*
Joly-Guillou, Clin Microbiol Infect 2005; 11: 868-873.*
Rathinavelu et al. Microbes and Infection 5 (2003) 651-657.*
Zavros et al. Infection and Immunity, May 2002, p. 2630-2639 vol. 70, No. 5.*
Sibbald et al., Microbiology and Molecular Biology Reviews, Sep. 2006, p. 755-788 vol. 70, No. 3).*
Killinen et al., Diabetologia (2006) 49: 66-70.*
Norton et al., FEMS Microbiology Letters, vol. 120, Issue 3, pp. 249-256.*
Brecker et al., Structural and immunological properties of arabinogalactan polysaccharides from pollen of timothy grass (*Phleum pratense* L.), Carbohydrate Research, 2005, vol. 340, pp. 657-663.
Cocoon Nutrition: "Quantum Adrenal Complex" XP002505224, Dec. 19, 2002.
Cortes-Perez, et al., Intranasal coadministration of live lactococci producing interleukin-12 and a major cow's milk allergen inhibits allergic reaction in mice, Clinical and Vaccine Immunology, Mar. 2007, vol. 14, Issue 3, pp. 226-233.
Currier et al., Effect over time of in-vivo administration of the polysaccharide arabinogalactan on immune and hemopoietic cell lineages in murine spleen and bone marrow, Phytomedicine, 2003, vol. 10, pp. 145-153.
Daniel et al., Modulation of allergic immune responses by mucosal application of recombinant lactic acid bacteria producing the major birch pollen allergen Bet v 1, Allergy, 2006, vol. 61, pp. 812-819.
Duan et al., Structural features of a pectic arabinogalactan with immunological activity from the leaves of Diospyros kaki, Carbohydrate Research, 2003, vol. 338, pp. 1291-1297.

(Continued)

Primary Examiner — Irene Marx
(74) Attorney, Agent, or Firm — Knobbe, Martens, Olson & Bear, LLP (57) ABSTRACT

The present invention relates to a pharmaceutical composition which includes naturally occurring, non-transgenic isolated bacteria from the group of *Lactococcus* and *Acinetobacter* or fragments thereof or mixtures thereof, to such a bacterium as a medicament for the prevention and/or treatment of allergic or chronic inflammatory disorders and to a process for producing this composition.

6 Claims, 4 Drawing Sheets

(56) References Cited

OTHER PUBLICATIONS

Huis In't Veld, J.H.J., De rol van melkzuurbacteriën bij voeding en gezondheid, Ned Tijdschr Tandheelkd, 1992, vol. 99, pp. 467-471.
Kelly, G.S., Larch arabinogalactan: Clinical relevance of a novel immune-enhancing polysaccharide, Alternative Medicine Review, 1999, vol. 4, Issue 2, pp. 96-103.
Kim et al., Immunological activity of larch arabinogalactan and echinacea: A preliminary, randomized, double-blind, placebo-controlled trial, Alternative Medicine Review, 2002, vol. 7, Issue 2, pp. 138-149.
Kimoto et al., New lactococcus strain with immunomodulatory activity: Enhancement of Th1-type immune response, Microbiol. Immunol., 2004, vol. 48, Issue 2, pp. 75-82.
Perdigon et al., Influence of the oral administration of lactic acid bacteria on IgA producing cells associated to bronchus, International Journal of Immunopathology and Pharmacology, 1999, vol. 12, Issue 2, pp. 97-102.
Perdigon et al., Study of the possible mechanisms involved in the mucosal immune system activation by lactic acid bacteria, J. Dairy Sci., 1999, vol. 82, Issue 6, pp. 1008-1114.
Taguchi et al., Structure of oligosaccharide side chains of an intestinal immune system modulating arabinogalactan isolated from rhizomes of Atractylodes lancea DC, Carbohydrate Research, 2004, vol. 339, pp. 763-770.
Villamil et al., Evaluation of immunomodulatory effects of lactic acid bacteria in turbot (*Scophthalmus maximus*), Clinical and Diagnostic Laboratory Immunology, Nov. 2002, vol. 9, Issue 6, pp. 1318-1323.
Vitini et al., Gut Mucosal immunostimulation by lactic acid bacteria, Biocell, 2000, vol. 24, Issue 3, pp. 223-232.
Ouwehand, A.E. 2007 "Antiallergic Effects of Probiotics" *The Journal of Nutrition* 137:794S-797S.
Wu, C. et al. 2006 "Immunomodulatory effects of IL-12 secreted by *Lactococcus lactis* on Th1/Th2 balance in ovalbumin (OVA)-induced asthma model mice" *international immunopharmacology* 6:610-615.
Proposals fro GRAS Register Inclusions 2006, retried from "http://www.foodsafety.govt.nz/elibrary/industry/gras/Proposals_Gras_Register_Inclusions_2006-.htm".
National Institute of Allergy and Infectious Diseases (NIAID) "Guidelines for the Diagnosis and Management of Food Allergy in the United States—Summary of the NIAID-sponsored Expert Panel Report", NIH publication No. 11-7700 Dec. 2010, One page.
Food Allergy from American Academy of Allergy Asthma and Immunology, retried from "http://www.aaaai.org/conditions-and-treatments/allergies/food-allergies.aspx" Oct. 27, 2011 accessed. One page.
Ngoc Ly P, Diane R. Gold, Arthur O. Tzianabos, Scott T. Weiss, Juan C. Celedon. Cytokines, allergy, and asthma, Current Opinion in Allergy and Clinical Immunology 2005; 5: 161-166.
El Biaze M, Boniface S, Koscher V, Mamessier E, Dupuy P, Milhe F et al. T cell activation, from atopy to asthma: more a paradox than a paradigm. Allergy 2003; 58(9):844-53.
Krug N, Madden J, Redington AE, Lackie P, Djukanovic R, Schauer U et al. T-cell cytokine profile evaluated at the single cell level in BAL and blood in allergic asthma. Am J Respir Cell Mol Biol 1996; 14(4):319-26.
Cho SH, Stanciu LA, Begishivili T, Bates PJ, Holgate ST, Johnston SL. Peripheral blood CD4+ and CD8+ T cell type 1 and type 2 cytokine production in atopic asthmatic and normal subjects. Clin Exp Allergy 2002; 32(3):427-33.
Boniface S, Koscher V, Mamessier E, El Biaze M, Dupuy P, Lorec AM et al. Assessment of T lymphocyte cytokine production in induced sputum from asthmatics: a flow cytometry study. Clin Exp Allergy 2003; 33(9):1238-43.
Cho SH, Stanciu LA, Holgate ST, Johnston SL. Increased interleukin-4, interleukin-5, and interferongamma in airway CD4+ and CD8+ T cells in atopic asthma. Am J Respir Crit Care Med 2005; 171(3):224-30.
Truyen E, Coteur L, Dilissen E, Overbergh L, Dupont LJ, Ceuppens JL et al. Evaluation of airway inflammation by quantitative Th1/Th2 cytokine mRNA measurement in sputum of asthma patients. Thorax 2006; 61(3):202-8.
Rowe J, Heaton T, Kusel M, Suriyaarachchi D, Serralha M, Holt BJ et al. High IFN-gamma production by CD8+ T cells and early sensitization among infants at high risk of atopy. J Allergy Clin Immunol 2004; 113(4):710-6.
Heaton T, Rowe J, Turner S, Aalberse RC, de Klerk N, Suriyaarachchi D et al. An immunoepidemiological approach to asthma: identification of in-vitro T-cell response patterns associated with different wheezing phenotypes in children. Lancet 2005; 365(9454):142-9.
Macaubas C, Sly PD, Burton P, Tiller K, Yabuhara A, Holt BJ et al. Regulation of T-helper cell responses to inhalant allergen during early childhood. Clin Exp Allergy 1999; 29(9):1223-31.
Smart JM, Kemp AS. Increased Th1 and Th2 allergen-induced cytokine responses in children with atopic disease. Clin. Exp Allergy 2002; 32(5):796-802.
Corrigan CJ, Kay AB. CD4 T-lymphocyte activation in acute severe asthma. Relationship to disease severity and atopic status. Am Rev Respir Dis 1990; 141(4 Pt 1):970-7.
Magnan AO, Mely LG, Camilla CA, Badier MM, Montero-Julian FA, Guillot CM et al. Assessment of the Th1/Th2 paradigm in whole blood in atopy and asthma. Increased IFN-gamma-producing CD8(+) T cells in asthma. Am J. Respir Crit Care Med 2000; 161(6):1790-6.
O'Sullivan S, Cormican L, Faul JL, Ichinohe S, Johnston SL, Burke CM et al. Activated, cytotoxic CD8(+) T lymphocytes contribute to the pathology of asthma death. Am J Respir Crit Care Med 2001; 164(4):560-4.
Yazdanbakhsh M, Kremsner PG, van Ree R. Allergy, parasites, and the hygiene hypothesis. Science 2002; 296: 490-494.
Oosterhout A.J.M. van and Motta A.C. Th1/Th2 paradigm: not seeing the forest for the trees? Eur. Respir. J. 2005; 25: 591-593.
Casalta Erick C. and Montel Marie-Christine. Safety assessment of dairy microorganisms: The Lactococcus genus. Int. J. Food Microbiol. 2008; 126: 271-273.
Salminen Seppo et al. Demonstration of safety of probiotics—a review. Int. J. Food. Microbiol. 1998; 44: 93-106.
Gandy, An Evaluation of the Anti-Allergic Properties of Potassium Humate, Dissertation (Jan. 2007) University of Pretoria, available at http://upetd.up.ac.za/thesis/available/etd-04292008-095801/unrestricted/dissertation.pdf.
International Search Report dated Dec. 18, 2009, for International Application No. PCT/EP2009/005911.
Showalter, A.M., "Arabinogalactan-proteins: structure, expression and function," Cell. Mol. Life Sci. (2001) 58, 1399-1417.
Su et al., "Purification and Characterization of a Novel Isoallergen of a Major Bermuda Grass Pollen Allergen, Cyn d 1," J. Biomed Sci (2003) 10, 111-119.
Strimas et al., "Significance of IgE level in amniotic fluid and cord blood for the prediction of allergy," Annals of Allergy (1988) 61, 133-136.
Office Action dated Sep. 26, 2014 for U.S. Appl. No. 14/059,180.
Fischer K, Stein K, Ulmer AJ, Lindner B, Heine H, and Hoist O. Cytokine-inducing lipoteichoic acids of the allergy-protective bacterium Lactococcus lactis G121 do not activate via Toll-like receptor 2. Glycobiology 2011; 21:1588-1595.
Schleifer KH, Kraus J, Dvorak C, Kilpper-Balz R, Collins MD, and Fischer W. Transfer of *Streptococcus lactis* and related streptococci to the genus Lactococcus gen. nov. System. Appl. Microbiol. 1985; 6:183-195.

\* cited by examiner

PHARMACEUTICAL COMPOSITION FOR PROTECTION FROM ALLERGIES AND INFLAMMATORY DISORDERS

CROSS-REFERENCE TO RELATED APPLICATIONS

This application claims the benefit of European Application No. 07 004 329.4, filed Mar. 2, 2007.

FIELD OF THE INVENTION

The present invention relates to a pharmaceutical composition which comprises naturally occurring, non-transgenic isolated bacteria from the group of *Lactococcus* and *Acinetobacter* or fragments thereof or mixtures thereof, to such a bacterium as medicament for the prevention and/or treatment of allergic or chronic inflammatory disorders and to a process for producing this composition.

DESCRIPTION OF THE RELATED ART

Excessive reactions of the body, especially of the immune system, to non-harmful foreign substances are referred to as allergies. These reactions proceed in exactly the same way as the normal immune response to a pathogen. Several types of allergic immune response are distinguished. Type I allergic reactions, which include bronchial asthma, atopic dermatitis, urticaria (nettle rash), hay fever and food allergies, are the most widespread. Although these diseases display different physical symptoms, the immunological mechanisms underlying them are similar.

Numerous studies demonstrate that allergic disorders are on the increase. The causes of the genesis and development of allergies are as yet unclear. Certain as yet unknown genetic factors and environmental conditions such as allergen exposure, living in towns, number of siblings and some infections probably contribute to the genesis.

Type I allergies are mediated by group E antibodies whose genesis depends on T-helper lymphocytes of group II. These Th2 cells occur more frequently in relation to the Th1 cells in allergies. Children are born initially with a Th2-dominated immune response which undergoes a transition in the first year of life, probably under the influence of microbial exposure, to a Th1-dominated response (nonallergic immune response). It is assumed that frequent infections correlate with a smaller Th2 response and thus fewer allergies. Low microbial exposure might thus lead to increased occurrence of allergies (hygiene hypothesis).

The possibilities for the prevention and therapy of allergic disorders are limited. Although the symptoms can be alleviated relatively well by numerous medicaments, the success of immunotherapeutic treatments such as desensitization varies. This therapy tends to be ineffective for example for the frequently occurring bronchial asthma. Nor does avoidance of allergens as preventive measure reliably contribute to reducing the incidence of allergies. Overall, there are no possibilities for reducing that risk of the development of allergies.

WO 01/49319 describes a composition which comprises antigens present on/in microorganisms and the use thereof for the prevention and treatment of allergic disorders. This composition is produced by collecting barn dust and suspending the latter where appropriate in a suitable solvent, e.g. water or isotonic saline. A suspension of microorganisms or else fragments of these organisms in a solvent is thus produced and can be administered directly or after further treatment steps for the treatment of allergies.

EP-A 1 637 147 describes an extract of barn dust for the treatment of allergic disorders, in which no heat input takes place throughout the production process, a process for its production and the use of this extract for producing a medicament for the treatment of allergic disorders.

WO 96/00579 describes a production process for producing a suspension and an extract of mycobacteria in aqueous solution, in which the extract is heated at 121° C. for at least 20 minutes. This suspension or this extract can be employed for nonspecific immunomodulation.

The use of *Lactococcus* species is described primarily for oral intake for probiotic purposes (for example Kimoto et al., *Microbiol. Immunol.* 2004; 48(2):75-82; Perdigon, G. et al., *Int. J. Immunopathol. Pharmacol.* 1999 May; 12(2):97-102; Villamil, L. et al., *Clin. Diagn. Lab. Immunol.* 2002 November; 9(6):1318-23; Vitini E. et al., *Biocell.* 2000 December; 24(3):223-32; Perdigon, G. et al. *J. Dairy. Sci.,* 1999 June; 82(6):1108-14; Huls in't Veid J H., *Ned. Tijdschr. Tandheelkd.* 1992 December; 99(12):467-70), as carrier for introducing recombinant genes but also whose expression may alleviate pathological conditions (Cortes-Perez, N. et al., *Clin. Vaccine Immunol.* Published online on 3 Jan. 2007; Daniel, C. et al., *Allergy,* 2006 July; 61(7):812-9; DE-A 101 01 793).

The use of *Lactococcus* sp. for the prevention and treatment of disorders is likewise described, specifically on oral intake for the prevention and treatment of obesity or diabetes (KR1020010106068), of gastric disorders (KR1020040044300) and of rheumatoid arthritis (EP-A 762 881). An antigen-antitoxin mixture for producing a homeopathic product whose main use is in the areas of cardiovascular disorders, hypertension and allergic conditions is described in DE-A 100 07 771.

SUMMARY OF THE INVENTION

The object of the present invention was to provide a mild composition for the prevention and treatment of allergic disorders and/or inflammatory disorders.

This object is achieved by a pharmaceutical composition comprising naturally occurring, non-transgenic, isolated bacteria selected from the group consisting of *Lactococcus* and *Acinetobacter* or fragments thereof or a mixture thereof and, where appropriate, a pharmaceutically acceptable carrier for the prevention and/or treatment of allergic or chronic inflammatory disorders selected from IgE-dependent type I allergies or type IV allergies.

BRIEF DESCRIPTION OF THE DRAWINGS

FIG. 3: Bacteria-induced cytokine pattern in human moDCs. (A) Human moDCs were stimulated for the period indicated in each case with LPS (10 ng/ml (circles)), with live *L. lactis* G121 ($10^6$ cfU/ml, triangles)) and live *A. lwoffii* F78 ($10^6$ cfU/ml, squares)). The TNF-α and IL-12p40 mRNA was determined in relation to HPRT by quantitative real-time PCR. The data represent an average of three independent experiments with moDCs from different healthy donors. (B) Treatment of human moDCs with LPS and increasing amounts of heat-inactivated bacteria. The TNF-α and IL-12p70 release was measured in the culture supernatant after incubation for 24 h.

FIG. 4: Both bacterial species induce a TH1-polarizing notch ligand expression in human moDCs. Human moDCs were stimulated for the stated period with LPS (10 ng/ml (circles)), with live *L. lactis* G121 ($10^6$ cfu/ml, triangles)) and live *A. lwoffii* F78 ($10^6$ cfu/ml, squares)). Delta-4 and Jagged-1 mRNA were measured using quantitative real-time PCR, and the data are shown as amounts of mRNA of the two genes in relation to HPRT. The data represent an average of three independent experiments with moDCs from different healthy donors.

DETAILED DESCRIPTION OF THE PREFERRED EMBODIMENT

One aspect of the present invention is the use of bacteria of the species *Lactococcus* and/or *Acinetobacter* as naturally occurring, non-genetically manipulated, in particular non-transgenic organisms. A further aspect is the use of the bacteria in isolated form. This means that either a *Lactococcus* species, preferably *Lactococcus lactis*, particularly preferably *Lactococcus lactis*, strain G121, and/or an *Acinetobacter* species, preferably *Acinetobacter lwoffii*, particularly preferably *Acinetobacter lwoffii*, strain F28, or a mixture of these two bacterial species are employed in previously isolated and, where appropriate, purified form in the pharmaceutical composition.

Said bacteria and/or mixtures thereof can also be employed directly as medicament for the prevention and/or treatment of allergic or chronic inflammatory disorders selected from IgE-dependent type I allergies or type IV allergies and chronic inflammatory cutaneous disorders or autoimmune diseases.

In a further embodiment of the invention, fragments of these bacteria are employed. Fragments preferably mean in the context of this invention membrane pieces and membrane constituents, cell wall proteins, in particular glycosylated proteins, polysaccharides, lipopolysaccharides (endotoxins), cytosolic proteins, molecules and/or compounds and/or metabolites secreted by the bacteria, nucleic acids and/or organelles. The fragments of the bacteria may also be employed at the same time as complete bacteria of the same or of the other species, that is mixed with the latter, or complete bacteria of one species and fragments of the other species can be employed.

The (unfragmented) bacteria can be used as medicament or employed in the pharmaceutical composition in the vital state or as killed bacteria. Since said bacteria are themselves completely harmless for mammalian organisms, use in the vital state is not problematic and corresponds to a preferred embodiment of the invention. In order to avoid contamination of the pharmaceutical composition with other, not so harmless microorganisms, however, it is also possible to apply a sterilization method directly, such as, for example, autoclaving, simple boiling or heating, the use of bactericides, bacteriostats, fungicides, fungistats, viricides and/or virostats, UV irradiation or the use of solvents which are not tolerated by the bacteria, such as, for example, alcohols, especially ethanol, propanol, isopropanol, etc., lyophilization or low-temperature sterilization.

A particular advantage of the present invention is the great efficacy while the routes by which the composition of the invention or the medicament of the invention can be administered are very simple. Administration is possible orally, nasally, conjunctivally, by inhalation, subcutaneously, intraarticularly, intraperitoneally, rectally or vaginally. Oral, nasal or inhalational administration is preferred.

A pharmaceutical composition according to the invention can be in the form of an aerosol, solution, preferably aqueous solution or hydroalcoholic solution, suspension, lyophilizate or powder. All these embodiments are particularly suitable for nasal, oral or inhalational administration of the bacteria and/or fragments thereof.

An aerosol of the invention preferably consists of small solid or liquid particles which can be generated by an inhaler, an atomizer or a ventilator. The particles of the aerosol may consist of the composition alone or of the composition in conjunction with a suitable carrier material. The aerosol may for example have a particle size of up to 100 μm for installational nasal use. For inhalational use, the aerosol may comprise for example particles of a particle size of up to 10 μm, preferably below 5 μm.

A solution of the invention comprising for example soluble fragments of said bacteria can preferably be an aqueous solution or a hydroalcoholic solution, for example a mixture of water or an aqueous solution with ethanol, propanol or isopropanol. The solution may for example be buffered or salt-containing, preferably isotonic, i.e. comprise buffer molecules or a physiological salt concentration. The solution may additionally comprise acceptable, e.g. natural or synthetic additives or excipients such as preservatives, stabilizers, odorants and flavorings, e.g. sugars, pharmaceutically acceptable carriers, emulsifiers, diluents and, if desired, acceptable colors.

In the case where complete bacteria or insoluble fragments and constituents thereof are used, they can be in the form of a suspension. A solution as previously described, or any other suitable suspending medium, can be used for the suspending.

The bacteria may also be in the form of a lyophilizate or be processed to a powder or incorporated into a pharmaceutically administrable powder. Such a lyophilizate or powder can be mixed with further pharmaceutically acceptable ingredients, in particular since it can be administered through a powder inhaler.

In a further preferred embodiment of the invention, a mixture of *Lactococcus* and *Acinetobacter* species, preferably a mixture of the abovementioned species and/or strains, is used as medicament or employed in a pharmaceutical composition. In the case of this embodiment, the bacterial species employed are mixed in a *Lactococcus:Acinetobacter* ratio of from 5:95 to 95:5, preferably 40:60 to 60:40, particularly preferably 50:50. The ratios are to be understood as approximate.

In a further embodiment of the invention, *Lactococcus* and/or *Acinetobacter* bacteria can also be employed in combination with one or more species of the following types of bacteria: *Micrococcus* spp., *Planococcus* spp., *Staphylococcus* spp., *Streptococcus* spp., *Lactococcus* spp., *Aerococcus* spp., *Gemella* spp., *Enterococcus* spp., *Bacillus* spp., *Clostridium* spp., *Micromonospora* spp., *Lactobacillus* spp., *Listeria* spp., *Erysipelothrix* spp., *Acinetobacter* spp., *Leuconostoc* spp., *Corynebacterium* spp., *Clavibacter* spp., *Brevibacterium* spp., *Propionibacterium* spp., *Arthrobacter* spp., *Curtobacterium* spp., *Microbacterium* spp., *Aureobacterium* spp., *Cellulomonas* spp., *Agromyces* spp., *Eubacterium* spp., *Pseudomonas* spp., *Xantomonas* spp., *Frateuria* spp., *Zoogloea* spp., *Escherichia* spp., *Enterobacter* spp., *Pantoea* spp., *Erwinia* spp., *Citrobacter* spp., *Klebsiella* spp., *Proteus* spp., *Serratia* spp., *Actinomyces* spp., *Streptomyces* spp., *Nocardia* spp., *Mycobacterium* spp., *Absidia* spp., *Wallemia* spp., *Eurotium* spp., *Acremonium* spp., *Aspergillus* spp., *Penicillium* spp., *Cladosporium* spp., *Cephalosporium* spp., *Fusarium* spp., *Mucor* spp., *Trichoderma* spp., or in combination with trichothecenes, fumonisins, gliotoxin, ochratoxins, patulin, aflatoxins.

A particular advantage of the use of the bacteria mentioned herein is that, owing to their own harmlessness, it is possible to carry out a particularly mild prevention or treatment. Said bacteria are ubiquitous in the environment, and no adverse effect on physical wellbeing or health is known. If the bacteria are employed before the occurrence of an allergic or inflammatory disorder, such a disease can be prevented, or the severity of the episode can be alleviated. This is generally referred to as "prevention". On use according to the invention of said bacteria it is possible to carry out such a prevention or else a treatment even during babyhood, or a prevention in utero by administration to pregnant women. The present mild possibility of prevention and treatment is to be particularly preferred especially when there is known to be a familial predisposition to allergies or (chronic) inflammatory disorders.

The present invention is particularly suitable for influencing the as yet unstimulated (naïve) and the child's immune system. The composition or the medicament can therefore be administered according to the invention repeatedly to pregnant women, babies and children in the first few years of life. The composition or the medicament is preferably administered to pregnant women, babies or children who, owing to a positive family history, have a distinctly increased risk of developing an allergic disorder. A positive family history can be assumed if at least one parent and/or at least one sibling or another close relative is already suffering from an allergic or chronic inflammatory disorder or shows symptoms thereof.

The composition of the invention or the medicament can also be employed for treating pregnant women, babies and children who already show the first signs of an allergic or chronic inflammatory disorder. An increased risk for a disorder can also be detected genetically.

The medicament or the composition can be administered for the treatment or prevention of children and adults. The medicament or the composition can be administered particularly preferably for prevention to pregnant women, babies or children, especially in the first few years of life, preferably in the first five years of life, particularly preferably in the first two years of life.

The composition is preferably administered using a conventional inhaler, nebulizer, atomizer or ventilator. It can be administered at regular intervals over a prolonged period in order to bring about a continuous stimulation in the organism. The composition can be administered 1 to 21 times a week, preferably 7 to 14 times a week, for example for up to 10 years. In this connection, depending on the treatment, a simple application (e.g. by spraying into the nose by means of a nebulizer) or, for example, prolonged inhalation is possible. In the latter case, the duration of each treatment can be between 1 to 120 min, preferably between 5 to 60 min.

Disorders which can be prevented in this mild and harmless way or which can be treated in this way are allergic or chronic inflammatory disorders selected from IgE-dependent type I allergies or type IV allergies and chronic inflammatory cutaneous disorders or autoimmune diseases, for example hay fever, food allergies, asthma, neurodermatitis, atopic dermatitis, contact eczema, psoriasis, type 1 and 2 diabetes, multiple sclerosis, collagenoses, rheumatoid arthritis, thyroid disorders such as Hashimoto's thyroiditis and Graves' disease.

The origin of the bacteria is immaterial to the pharmaceutical composition of the invention or to the use of said bacteria as medicament. The bacteria can be isolated from a natural source such as grass, hay, house dust, barn dust, foodstuffs or the like and, where appropriate, purified and grown in culture, or they can be obtained commercially as single cultures.

Production Process

To produce a pharmaceutical composition according to the invention, *Lactococcus* bacteria and/or *Acinetobacter* bacteria, preferably *Lactococcus lactis* and/or *Acinetobacter lwoffii*, particularly preferably *Lactococcus lactis*, G121 and/or *Acinetobacter lwoffii* F78 are either isolated from a natural source or obtained commercially and grown in culture. For example, the bacteria can be isolated from barn dust and grown under suitable culturing conditions as described in example 1.

After the bacteria have been harvested they can be either directly taken up in an aqueous or hydroalcoholic medium in order to obtain a bacterial suspension, or they can previously undergo a fragmentation step. Suitable methods for fragmentation are known to those skilled in this art and include for example chemical lysis methods, pressure/decompression (e.g. using the so-called French press), mechanical methods or ultrasound, to name some disruption methods. This can also be followed by a specific purification method, for example when some constituents of the cells are unwanted in the pharmaceutical composition. For example, nucleic acids can be removed selectively.

As alternative to fragmentation, or else in addition thereto, a bacteria-killing step can be carried out. Any known and suitable method can be used for this purpose, such as, for example, autoclaving, boiling, application of heat, radiation (UV, radioactive), the use of bactericides, bacteriostats, fungicides, fungistats, viricides and/or virostats, or the use of solvents which are not tolerated by the bacteria, such as, for example, alcohols, especially ethanol, propanol, isopropanol etc. or low-temperature sterilization.

The vital or killed bacteria obtained from the aforementioned steps, or the fragments obtained therefrom can be used directly as medicament, be incorporated into one, or be mixed with (a) pharmaceutical carrier(s) and excipient(s) in order to provide them in the form of an aerosol, of a solution or of a suspension.

A particularly preferred process step which can optionally be carried out is drying or lyophilization (freeze drying) of the vital or killed bacteria or of the fragments obtained therefrom. It is also possible for stabilization during the lyophilization to add for example sucrose, dextran or glycerol. The dried product or lyophilizate produced in this way can then be employed directly as medicament or be mixed with pharmaceutically acceptable adjuvants and processed for example to an inhalable powder.

The pharmaceutically acceptable carrier may be water, a buffer or salt solution, preferably a physiological saline solution, an alcohol or a hydroalcoholic mixture, or a pharmaceutically acceptable powder such as, for example, a finely ground silicate, starch, cellulose and cellulose derivatives and many others. Use takes place inter alia as aerosol by means of an atomizer or nebulizer, a compressed gas aerosol by means of a vibrating orifice generator or a spinning disk generator or a powder inhalation by means of conventional nebulizer systems such as one- or two-fluid nozzles.

EXAMPLE 1

Isolation and Characterization of the Strains

The bacterial strains *L. lactis* G121 and *A. lwoffii* F78 were isolated after culturing of dust samples collected from animal houses in Bavaria, Germany and were further cultured. *Acinetobacter lwoffii* F78 was grown in SB medium (10 g of Mops, 20 g of yeast extract, 30 g of Tryptone in 1 liter, completed with 10 ml of 2 M glucose after autoclaving) and *Lactococcus lactis* G121 was grown in TSB medium which contained 0.3% yeast extract. The culturing conditions for both strains were 30° C. up to the required cell density (within the logarithmic phase).

The strains were characterized with the aid of a specific PCR for sequencing the 16S rDNA. The PCR primers were selected on the basis of conserved regions of *A. lwoffii* F78 and *L. lactis* G121. For amplification of the 16S rDNA, single colonies were transferred into a PCR vessel, mixed with PCR reaction mixture (35 µl of $H_2O$, 5 µl of 10× Advantage 2 PCR buffer (Clontech, Saint-Germain-en-Laye, France), 2.5 µl of each primer solution (final concentration 10 µM/ml), 1 µl of each dNTP (dNTP set PCR grade; Invitrogen, Karlsruhe, Germany) and 1 µl of 50× Advantage 2 polymerase mix (Clontech)). The PCR was carried out with the following conditions: 1 min 95° C., followed by 40 (*A. lwoffii*) or 30 (*L. lactis*) cycles with 20 s at 95° C., 30 s at 60° C. and 1.5 min at 72° C. The reactions were terminated with a last filling-in step at 72° C. for 7 min. The amplification products were analyzed in a 2% agarose gel, isolated from the gel and purified (Qiaquick PCR purification Kit, Qiagen, Hilden, Germany) and sequenced. The primers used are to be found in table 1. Primers 1, 2, 5 and 6 are PCR primers, primers 3, 4 and 7 to 10 are sequencing primers.

TABLE 1

| Number | Primer | Sequence (5'→3') | |
|---|---|---|---|
| 1 | 5 Aci 16S | ACACATGCAAGTCGAG | (SEQ ID NO: 1) |
| 2 | 3 Aci 16S | CTACTTCTGGTGCAACA | (SEQ ID NO: 2) |
| 3 | Aci 16S | CCTAATACATGCAAGT | (SEQ ID NO: 3) |
| 4 | Aci 16S | GCTACCTTGTTACGACT | (SEQ ID NO: 4) |
| 5 | 5 Lacto 16S | ACCGGCTAACTCTGTG | (SEQ ID NO: 5) |
| 6 | 3 Lacto 16S | TTCACCGCTACACCTGG | (SEQ ID NO: 6) |
| 7 | Lacto SeqPri | TGCATTGGAAACTGGT | (SEQ ID NO: 7) |
| 8 | Lacto SeqPri | GTGCATGGTTGTCGTCA | (SEQ ID NO: 8) |
| 9 | Lacto SeqPri | GGAATAGCACGAGTAT | (SEQ ID NO: 9) |
| 10 | Lacto SeqPri | TCAGTTACAGGCCAGA | (SEQ ID NO: 10) |

EXAMPLE 2

Efficacy In Vivo

The complete protective potency of the composition of the invention was determined in vivo by immunological and cytobiological functional investigations in the standardized animal model of the mouse.

Firstly described below are the methods for sensitizing and inducing allergic asthma in mice with ovalbumin, of treatment with *Lactococcus* and/or *Acinetobacter* bacteria and of analysis of the allergic and inflammatory reactions.

2.1. Sensitization and induction of allergic asthma in mice with ovalbumin (OVA)—Aluminum hydroxide (Pierce) was used as adjuvant for sensitizing mice against the model allergen ovalbumin. It is known that this adjuvant induces immune responses which are characterized by production of cytokines such as IL-4, IL-5 and IL-13 and by the production of antibodies of the IgE and IgG1 isotype (the corresponding isotype in humans is IgG4). Sensitization of six- to eight-week old mice of the inbred strain Balb/c took place by intraperitoneal injection of a mixture of 10 µg of ovalbumin (grade V from Sigma) and 1.5 mg of aluminum hydroxide in a total volume of 200 µl of buffer (PBS). The injection took place three times in total, namely on day 0, on day 14 and on day 21.

In order subsequently to elicit an allergic reaction in the lung of the mice, that is to say to induce the acute allergic asthma, the mice were treated on each of day 22, 27 and day 28 with ovalbumin in aerosol for 20 minutes. For this purpose, the mice were placed in a Plexiglas chamber with a volume of 1 l liters. A Pari inhaler was connected to the chamber and had previously been charged with 1% strength ovalbumin solution and was operated with a Pari-Boy turbo aerosol generator. After the second administration of OVA aerosol it was possible to diagnose symptoms of acute allergic asthma in the mice for some days. The symptoms included:

1) increased response to methacholine, bronchial hyperreactivity;
2) increased infiltration of eosinophilic granulocytes and lymphocytes into the airway lumen;
3) production of ovalbumin-specific antibodies of the IgE and IgG1 isotypes;
4) production of interleukin-5 following in vitro restimulation of lymphocytes with ovalbumin.

The methods for measuring individual parameters are explained in detail below.

2.2. Measurement of the bronchial hyperreactivity—A decisive diagnostic parameter measured in humans in order to diagnose an allergic asthmatic disorder reliably is the bronchial hyperreactivity. This takes the form of a hypersensitivity of the smooth muscles of the bronchi to nonspecific irritations. For the diagnosis in humans, low concentrations of histamine are administered and then the airway resistance is measured in a plethysmograph. Asthmatic people show a greater bronchoconstriction which depends on the histamine concentration, and thus a higher airway resistance than healthy people.

The measurement in mice took place in a very similar way. For the measurement, the mice were placed in the chambers provided for this purpose in a Buxco plethysmograph. A continuous stream of air flowed through the chambers, and a highly sensitive pressure transducer recorded short-term changes in pressure in the chamber. Inhalation by the mice generated a reduced pressure and exhalation generated a raised pressure in the chamber. These changes in pressure were recorded continuously as a function of time, and the so-called Penh value was calculated by the software from the measured values for each breathing cycle. This dimensionless value correlates with the airway resistance. In hyperreactive mice, the airway resistance was increased as a function of the methacholine concentration (methacholine is used for provocation in mice instead of histamine, because the bronchi of mice do not respond to histamine), as expressed by the increase in the Penh value.

The bronchial hyperreactivity was measured 24 hours after the last exposure to OVA aerosol. For measurement of the bronchial hyperreactivity, an adaptation period of 10 minutes was followed by the mice being brought into contact with PBS aerosol in the plethysmograph for 7 minutes, during which the Penh value was recorded. This was followed by exposure for 7 minutes in each case to increasing concentrations of methacholine: 6, 12, 25, 50 mg/ml. The Penh value was continuously measured during each exposure and is averaged over periods of 30 seconds. The period in which the maximum Penh value was reached for a particular methacholine concentration was then plotted against the methacholine concentration. This resulted in a dose-effect plot whose area under the curve increased as the strength of the reaction of the mice to methacholine increases. The area under the curve thus correlated with the hyperreactivity of the animals and was used for statistical analysis.

2.3. Investigation of the cellular composition of the bronchio-alveolar lavage (BAL)—Only very few or no eosinophilic granulocytes could be observed in the lung tissue and in the lumen of the airways of healthy subjects and untreated mice. The leukocytes found in healthy airways are mainly macrophages. In connection with allergic asthma there is, for reasons which have not been entirely explained, massive infiltration of the airways by eosinophilic granulocytes and to a smaller extent by lymphocytes.

In order to investigate the composition of the leukocyte infiltrate in the airways of mice, they were sacrificed three days after the last exposure to OVA aerosol. The trachea was exposed and a 24 G indwelling vein cannula was inserted into the trachea. The lumen of the airways was washed through this twice with 1 ml of isotonic buffer each time (bronchio-alveolar lavage). The total number of cells rinsed out of the lung in this way was counted microscopically using a Neubauer counting chamber. The leukocytes of the BAL were then centrifuged onto slides with a Shandon cyto-centrifuge. The cells were then stained with the HAEME fast staining kit from Labor+Technik Eberhard Lehmann, as described in the product leaflet. After the staining had taken place, 300 cells on the slide were counted microscopically and classified according to conventional criteria into the various leukocyte subpopulations. The percentage composition of the BAL could then be calculated.

2.4. Measurement of OVA-specific antibodies of the IgE and IgG1 isotype—Sensitization to an allergen can be measured by determining allergen-specific antibodies of the IgG1 and IgE classes. The allergen-specific antibodies were quantified in mouse serum by indirect ELISA. For this purpose, blood was taken from the tail vein of the mice two days after the last administration of OVA aerosol. After the blood had clotted, the serum was obtained by centrifugation and employed in the ELISA.

Brief instructions for ELISA:
IgE (OVA-spec.) ELISA:
Coat plates with 5 µg/ml OVA in coating buffer, in each case 100 µl per depot (overnight)
Wash 3×, 250 µl per depot each time
Over-coating with 1% BSA in washing buffer, 250 µl per depot, 1 hour
Wash 3×
Load serum dilutions in washing buffer ⅓ 1/10 and 1/30, 100 µl per depot, 1 hour
Wash 3×
Load biotinylated anti-IgE antibody (Pharmingen, R35-72) diluted 1/100 in washing buffer, 100 µl per depot, 1 hour
Wash 3×
Load extravidin-POD (Sigma) diluted 1/1000 in washing buffer, 100l per depot, 1 hour
Wash 3×
Load TMB substrate solution, 100 µl per depot, 30 min
Stop reaction with 50 µl of 1M sulfuric acid per depot, plate can be measured at a wavelength of 450 nm
IgG1 (OVA-spec.) ELISA:
Coat plates with 5 µg/ml OVA in coating buffer, in each case 100 µl per depot (overnight)
Wash 3×, 250 µl per depot each time
Over-coating with 5% MMP in washing buffer, 250 µl per depot, 1 hour
Wash 3×
Load serum dilutions in dilution buffer 1/100 1/300 1/1000 and 1/3000, 100 µl per depot, 1 hour
Wash 3×
Load AKP-conjugated anti-IgG1 antibody (Pharmingen, ×56) diluted 1/1000 in dilution buffer, 100 µl per depot, 1 hour
Wash 3×
Load pNPP substrate solution, 100 µl per depot, 30 min
Stop reaction with 50 µl of 1M sodium hydroxide solution per depot, plate can be measured at a wavelength of 405 nm
Serial dilutions of a standard serum were included on each ELISA plate. A known concentration of OVA-specific antibodies of the IgG1 and IgE isotype was present in this standard serum. The concentration in the unknown sample can be calculated by comparing measurements from mouse serum with unknown OVA-spec. IgG1 and IgE concentration with the series of measurements on the known mouse serum.

2.5. Treatment of mice with *Lactococcus lactis* and *Acinetobacte lwoffii* during sensitization:—Mice were treated with the two bacterial strains *Lactoccus lactis* G121 and *Acinetobacter lwoffii* F78 by administering to them intranasally $10^8$ cfu lyophilized bacteria, or PBS as control, in each case in the anesthetized state, every second day, starting 10 days before the first sensitization, over the entire period of the sensitization phase and induction phase (see above: "Sensitization and induction of allergic asthma in mice with ovalbumin (OVA)").

2.6. Formation and stimulation of human dendritic cells derived from monocytes (moDCs)—Heparinized blood from healthy donors was produced with the aid of the Ficoll (PAA Laboratories GmbH, Pasching, Austria) separation method, and the peripheral mononuclear cells (PBMCs) were obtained. Subsequently, the monocytes were isolated by counterflow elutriation centrifugation. The moDCs were then prepared as described by Sallusto & Lanzavecchia, *J. Exp. Med.* 1994; 179:1109-1119. Briefly summarized, this method can be described as follows: Monocytes (95% purity) were cultured at $10^6$ cell/ml in RPMI 1640 (Cambrex, East Rutherford, USA), supplemented with 10% heat-inactivated fetal calf serum (Biochrom AG, Berlin, Germany), 100 U/ml penicillin (PAA Laboratories GmbH), 100 µg/ml streptomycin (PAA Laboratories GmbH), 500 U/ml GM-CSF (Strathmann Biotec GmbH, Hamburg, Germany) and 500 U/ml IL-4 ((Strathmann Biotec GmbH), with half of the medium including the cytokines being exchanged every 2 to 3 days. On day 7, the cells were harvested and cultured further in complete medium at a density of $10^6$ cells/ml in 24-well plates. The cells were either left untreated or treated with 10 ng/ml LPS from *Salmonella enterica* sv. Friedenau or $10^6$ cfu/ml *L. lactis* G121 or *A. lwoffii* F78.

2.7. Expression of co-stimulating molecules in human moDCs—After incubation with the stimuli indicated in section 2.6 for 24 h, the cells were harvested and brought into contact with fluorochrome-conjugated monoclonal antibodies (mAbs) for CD40, CD80, CD86 or MHC class II, and fixed with 1.5% paraformaldehyde. The mAbs for CD40-PE and CD80-PE, MHC class II-PE, IgG1- and IgG2a-PE were purchased from BeckmannCoulter (Fullerton, USA), the CD86-PE mAB was purchased from BD PahrMingen (San Diego, USA). The cells were analyzed by flow cytometry in a FACSCalibur using the CellQuest program (Becton Dickinson, San Jose, USA).

2.8. Real-time quantitative PCR—After incubation with the abovementioned stimuli for 3, 6 and 12 h, total RNA was isolated from the moDCs using the Absolutely RNA kit from Stratagene and underwent reverse transcription into cDNA using oligo(dT)12-18 and Superscript reverse transcriptase (invitrogen). The transcripts were quantified by quantitative real-time PCR in a LightCycler 2.0 using the FastStart DNA Master Plus SYBR Green kit (Roche Applied Science, Mannheim, Germany) in accordance with the manufacturer's instructions. For each sample, the specific mRNA occurrence was normalized to the amount of HPRT mRNA and rendered in freely chosen units. The real-time PCRs were carried out with the primers rendered in table 2 below:

TABLE 2

| Primer | Sequence (5'→3') | |
|---|---|---|
| HPRT-for | GTCAGGCAGTATAATC | (SEQ ID NO: 11) |
| HPRT-rev | GGGCATATCCTACAAC | (SEQ ID NO: 12) |
| TNFα-for | CCTGTAGCCCATGTTGT | (SEQ ID NO: 13) |
| TNFα-rev | TTGAAGAGGACCTGGG | (SEQ ID NO: 14) |
| IL-12p40-for | AAAGGAAGATGGAATT | (SEQ ID NO: 15) |
| IL-12p40-rev | TGCTGCTTTTGACACTG | (SEQ ID NO: 16) |
| Delta-4-for | GGCCTGTTTTGTGACCA | (SEQ ID NO: 17) |
| Delta-4-rev | CGACAGGTGCAGGTGT | (SEQ ID NO: 18) |
| Jagged-1-for | CTGGCGGCTGGGAAGG | (SEQ ID NO: 19) |
| Jagged-1-rev | GAGGGCTGCAGTCATT | (SEQ ID NO: 20) |

EXAMPLE 3

Figure 1:
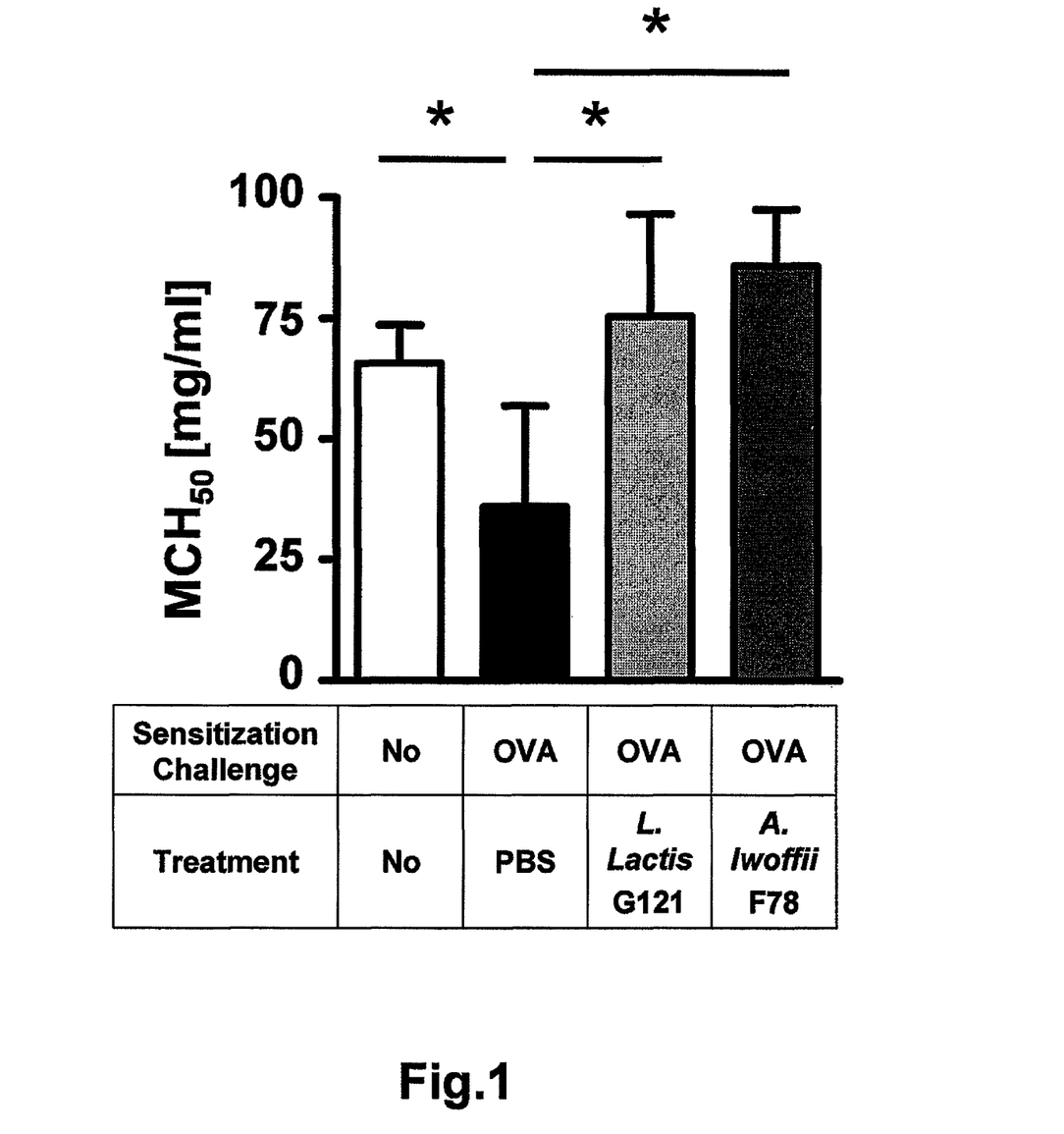
FIG. 1: Intranasal treatment with *L. lactis* G121 and *A. lwoffii* F78 improves the reactivity of the airways to methacholine in allergic mice. The mice were treated as described in section 2.2. below. Pulmonary function was analyzed as described. An average significant difference (□SD) of the methacholine concentration which brought about a 50% reduction in the average expiratory airflow (MCH50) in eight mice per group is indicated. Significant differences with $p<0.05$ are characterized by an *

Results of the In Vivo Experiments 3.1. Asthma symptoms—The experiment which goes furthest to demonstrate the biological effect of the bacteria as medicament or in a pharmaceutical composition of the invention is investigation of the asthma symptoms induced by allergy in the mice. FIG. 1 shows that a marked improvement in the respiratory activity can be achieved in the asthmatic mice by treatment with the bacteria *Lactococcus lactis* G121 and *Acinetobacter lwoffii* F78, and a methacholine concentration which brought about a 50% reduction in the average expiratory airflow ($MCH_{50}$) in eight mice per group is in fact higher than the level of untreated mice without asthma.

Figure 2:
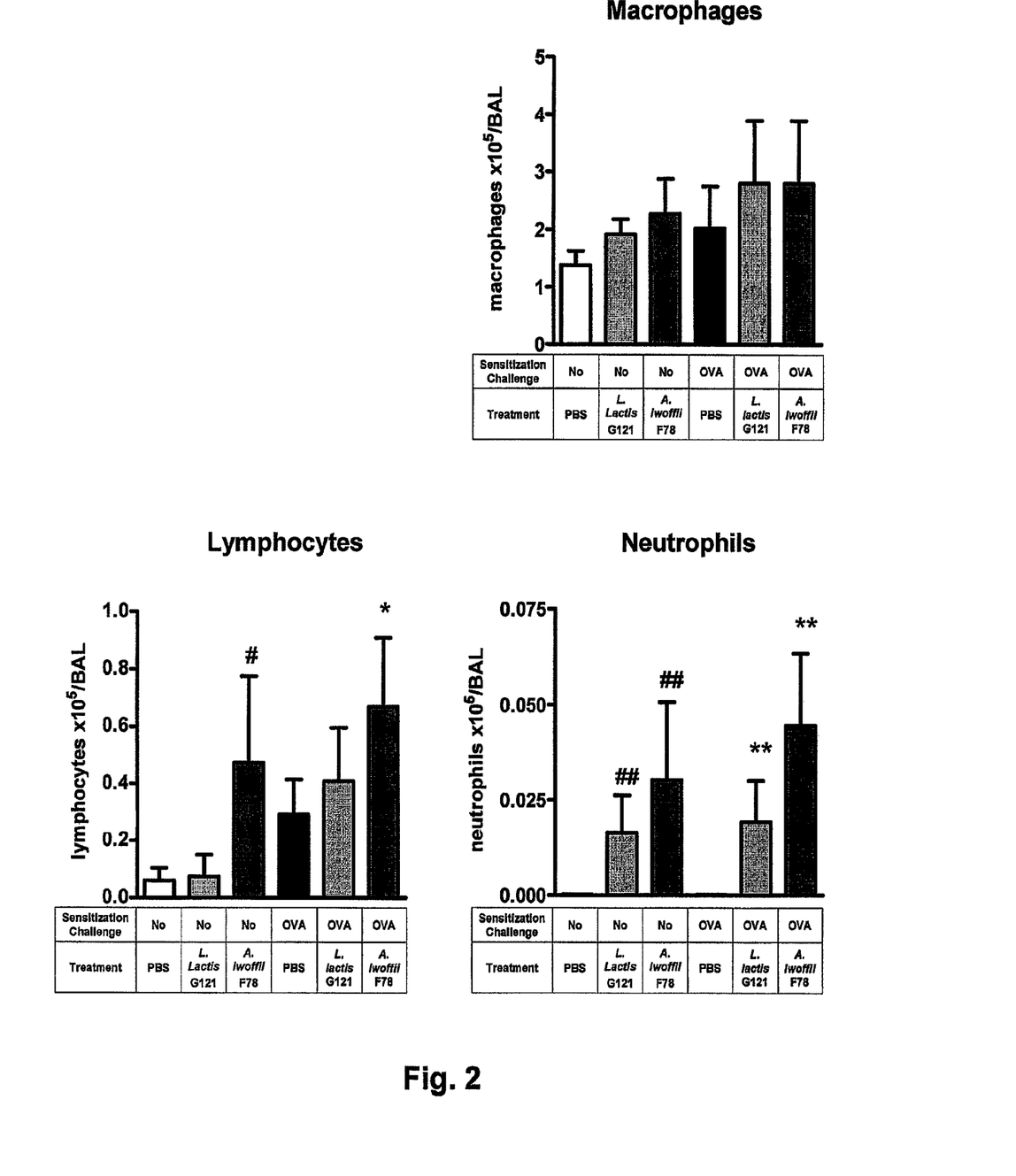
FIG. 2: Inhibition of eosinophil infiltration by i.n. treatment of mice with *L. lactis* G121 and *A. lwoffii* F78. Groups of mice (each n=6) were treated i.n. either with PBS, *L. lactis* G121 or *A. lwoffii* F78, sensitized and exposed to OVA, or remained unsensitized/without OVA, as described below in section 2.3. The number of eosinophils, lymphocytes, macrophages and neutrophils was analyzed in the BAL by microscopic determination. The results are shown as average significant difference (□SD). Significant differences from the nonsensitized PBS-treated control group are indicated by #, and from the sensitized PBS-treated group by an * with $p<0.05$ (#,*), $p<0.01$ (##,) or $p<0.001$ (*).

3.2. Inflammation in the bronchi—Eosinophilic cells in the bronchi of mice with asthma reflect the condition of an asthmatic inflammation. FIG. 2 demonstrates that treatment of the mice with the bacteria *L. lactis* G121 and *A. lwoffii* F78 greatly diminished the number of eosinophilic cells, which were greatly raised in diseased mice and were absent in the normal case, and only few are now to be found.

3.3. Allergic sensitization—The asthma symptoms are induced in the mice by sensitization with an allergen. It was therefore investigated whether the IgG1 antibodies against the allergen which increase on sensitization are influenced by the bacterial administration according to the invention. The table demonstrates that the IgG1 antibodies directed against ovalbumin decreased on use of the bacteria *L. lactis* G121 and *A. lwoffii* F78 compared with untreated mice. The increase in IgG1 antibodies on ovalbumin sensitization reflected a reaction of the T lymphocytes of the helper-2 type (Th2), an increase of which is to be observed in allergies. In this connection, table 3 shows that administration of the bacteria was associated with a decrease in the antibody concentration.

TABLE 3

| | Sensitization | | | |
|---|---|---|---|---|
| | none | OVA | OVA | OVA |
| | | | Treatment | |
| | none | PBS | *L. lactis* G121 | *A. lwoffii* F78 |
| OVAIGE [ng/ml] | 0 | 3.5 ± 1.5 | 3.9 ± 0.7 | 4.0 ± 1.5 |
| OVAIgG1 [mg/ml] | 0 | 3.8 ± 1.2 | 2.2 ± 1.2 | 2.5 ± 1.8 |
| OVAIgH2a [ng/ml] | 0 | 321 ± 265 | 418 ± 264 | 245 ± 278 |

3.4. Stimulation of moDCs. moDCs brought into contact with the bacteria were stimulated by addition of the bacteria to CD40 and CD86 synthesis (FACS data not shown), specifically on stimulation with *A. lwoffii* F78 even at a concentration of about $10^2$ to $10^3$ cfu/ml, and with *L. lactis* G121 at a concentration of about $10^4$ cfU/ml.

Figure 3:
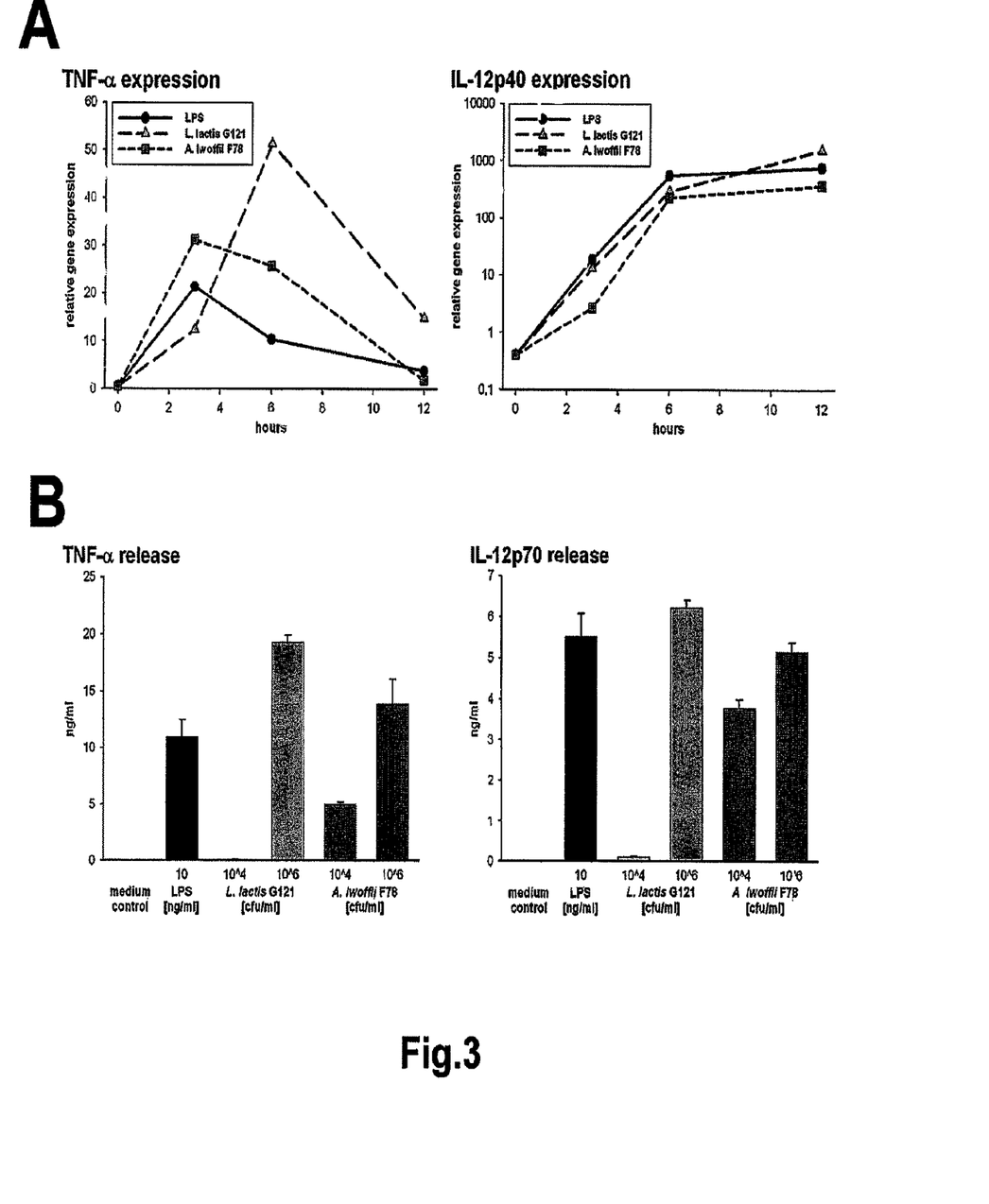

The expression of TNFα and IL-12 after stimulation with LPS, *L. lactis* G121 and *A. lwoffii* F78 was investigated at the mRNA level. The results are shown in FIG. 3a. The increased expression also led to an increase in the release of the cytokines by the cells (FIG. 3b).

Figure 4:
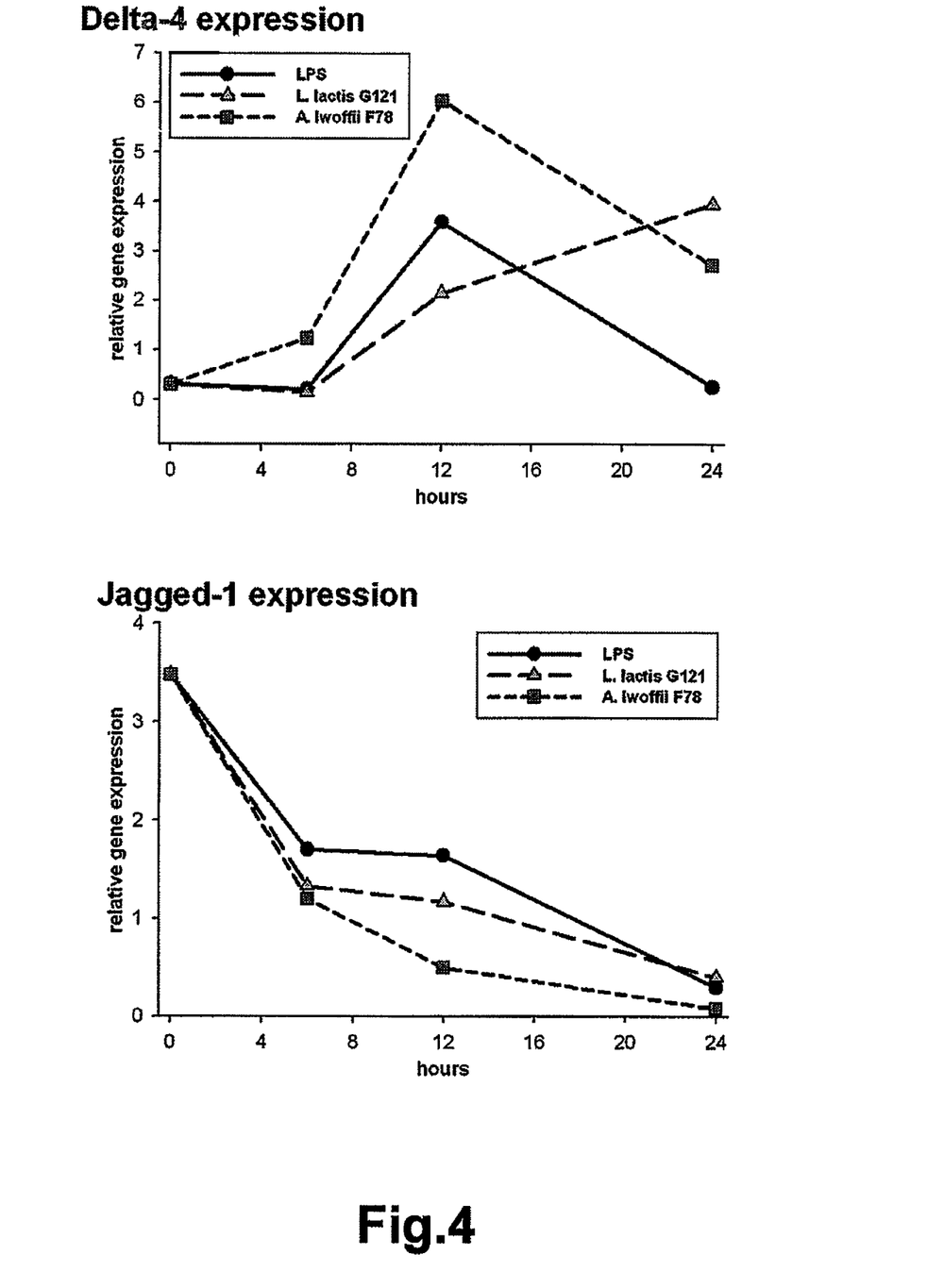

In order to test the ability of the bacteria to modulate the T-helper cell polarization, the expression of notch ligands on dendritic cells was investigated after stimulation with the bacteria. Two groups of notch ligands are expressed by dendritic cells, and the ratio thereof is important for polarization of T-helper cells: the delta group guides T-cell polarization in the direction of TH1, while the Jagged group induces TH2 responses. It is evident from FIG. 4 that stimulation of the cells with the bacteria brings about a marked increase in delta-4 expression with a simultaneous reduction in Jagged expression.

What is claimed is:

1. A method for reduction of the likelihood of occurrence in a human subject of an allergic or chronic inflammatory disorder selected from the group consisting of IgE-dependent type I allergies to at least one antigen, type IV allergies to at least one antigen, chronic inflammatory cutaneous disorders resulting from an allergy to at least one antigen and autoimmune diseases directed against at least one antigen comprising:

administering intranasally to the human subject in the first two years of life before symptoms of said allergic or chronic inflammatory disorder occur, an effective amount of a pharmaceutical composition consisting essentially of a naturally occurring, non-transgenic, isolated *Lactococcus* bacteria strain known to have no adverse effect on physical wellness or on health from 1 to 21 times a week.

2. The method as claimed in claim 1, wherein said pharmaceutical composition is in the form of an aerosol, aqueous solution, suspension, lyophilizate or powder.

3. The method as claimed in claim 1, wherein said bacteria are *Lactococcus lactis*.

4. The method as claimed in claim 1, wherein said bacteria are in the vital or killed state.

5. The method as claimed in claim 1, wherein said allergic or chronic inflammatory disorder is selected from the group consisting of hay fever, food allergies, asthma, neurodermatitis, and atopic dermatitis.

6. The method as claimed in claim 1, wherein said pharmaceutical composition is suitable for reduction of the likelihood of allergic or chronic inflammatory disorders in babies or children who, owing to a positive family history, have a distinctly increased risk of developing such a disorder.

* * * * *

SEQUENCE LISTING

<160> NUMBER OF SEQ ID NOS: 20

<210> SEQ ID NO 1
<211> LENGTH: 16
<212> TYPE: DNA
<213> ORGANISM: Artificial Sequence
<220> FEATURE:
<223> OTHER INFORMATION: synthetic primer

<400> SEQUENCE: 1
acacatgcaa gtcgag                                                        16

<210> SEQ ID NO 2
<211> LENGTH: 17
<212> TYPE: DNA
<213> ORGANISM: Artificial Sequence
<220> FEATURE:
<223> OTHER INFORMATION: synthetic primer

<400> SEQUENCE: 2
ctacttctgg tgcaaca                                                       17

<210> SEQ ID NO 3
<211> LENGTH: 16
<212> TYPE: DNA
<213> ORGANISM: Artificial Sequence
<220> FEATURE:
<223> OTHER INFORMATION: synthetic primer

<400> SEQUENCE: 3
cctaatacat gcaagt                                                        16

<210> SEQ ID NO 4
<211> LENGTH: 17
<212> TYPE: DNA
<213> ORGANISM: Artificial Sequence
<220> FEATURE:
<223> OTHER INFORMATION: synthetic primer

<400> SEQUENCE: 4
gctaccttgt tacgact                                                       17

<210> SEQ ID NO 5
<211> LENGTH: 16
<212> TYPE: DNA
<213> ORGANISM: Artificial Sequence
<220> FEATURE:
<223> OTHER INFORMATION: synthetic primer

<400> SEQUENCE: 5
accggctaac tctgtg                                                        16

<210> SEQ ID NO 6
<211> LENGTH: 17
<212> TYPE: DNA
<213> ORGANISM: Artificial Sequence
<220> FEATURE:
<223> OTHER INFORMATION: synthetic primer

<400> SEQUENCE: 6
ttcaccgcta cacctgg                                                       17

<210> SEQ ID NO 7
<211> LENGTH: 16
<212> TYPE: DNA
<213> ORGANISM: Artificial Sequence

```
<220> FEATURE:
<223> OTHER INFORMATION: synthetic primer

<400> SEQUENCE: 7
tgcattggaa actggt                                              16

<210> SEQ ID NO 8
<211> LENGTH: 17
<212> TYPE: DNA
<213> ORGANISM: Artificial Sequence
<220> FEATURE:
<223> OTHER INFORMATION: synthetic primer

<400> SEQUENCE: 8
gtgcatggtt gtcgtca                                             17

<210> SEQ ID NO 9
<211> LENGTH: 16
<212> TYPE: DNA
<213> ORGANISM: Artificial Sequence
<220> FEATURE:
<223> OTHER INFORMATION: synthetic primer

<400> SEQUENCE: 9
ggaatagcac gagtat                                              16

<210> SEQ ID NO 10
<211> LENGTH: 16
<212> TYPE: DNA
<213> ORGANISM: Artificial Sequence
<220> FEATURE:
<223> OTHER INFORMATION: synthetic primer

<400> SEQUENCE: 10
tcagttacag gccaga                                              16

<210> SEQ ID NO 11
<211> LENGTH: 16
<212> TYPE: DNA
<213> ORGANISM: Artificial Sequence
<220> FEATURE:
<223> OTHER INFORMATION: synthetic primer

<400> SEQUENCE: 11
gtcaggcagt ataatc                                              16

<210> SEQ ID NO 12
<211> LENGTH: 16
<212> TYPE: DNA
<213> ORGANISM: Artificial Sequence
<220> FEATURE:
<223> OTHER INFORMATION: synthetic primer

<400> SEQUENCE: 12
gggcatatcc tacaac                                              16

<210> SEQ ID NO 13
<211> LENGTH: 17
<212> TYPE: DNA
<213> ORGANISM: Artificial Sequence
<220> FEATURE:
<223> OTHER INFORMATION: synthetic primer

<400> SEQUENCE: 13
cctgtagccc atgttgt                                             17
```

```
<210> SEQ ID NO 14
<211> LENGTH: 16
<212> TYPE: DNA
<213> ORGANISM: Artificial Sequence
<220> FEATURE:
<223> OTHER INFORMATION: synthetic primer

<400> SEQUENCE: 14
ttgaagagga cctggg                                                     16

<210> SEQ ID NO 15
<211> LENGTH: 16
<212> TYPE: DNA
<213> ORGANISM: Artificial Sequence
<220> FEATURE:
<223> OTHER INFORMATION: synthetic primer

<400> SEQUENCE: 15
aaaggaagat ggaatt                                                     16

<210> SEQ ID NO 16
<211> LENGTH: 17
<212> TYPE: DNA
<213> ORGANISM: Artificial Sequence
<220> FEATURE:
<223> OTHER INFORMATION: synthetic primer

<400> SEQUENCE: 16
tgctgctttt gacactg                                                    17

<210> SEQ ID NO 17
<211> LENGTH: 17
<212> TYPE: DNA
<213> ORGANISM: Artificial Sequence
<220> FEATURE:
<223> OTHER INFORMATION: synthetic primer

<400> SEQUENCE: 17
ggcctgtttt gtgacca                                                    17

<210> SEQ ID NO 18
<211> LENGTH: 16
<212> TYPE: DNA
<213> ORGANISM: Artificial Sequence
<220> FEATURE:
<223> OTHER INFORMATION: synthetic primer

<400> SEQUENCE: 18
cgacaggtgc aggtgt                                                     16

<210> SEQ ID NO 19
<211> LENGTH: 16
<212> TYPE: DNA
<213> ORGANISM: Artificial Sequence
<220> FEATURE:
<223> OTHER INFORMATION: synthetic primer

<400> SEQUENCE: 19
ctggcggctg ggaagg                                                     16

<210> SEQ ID NO 20
<211> LENGTH: 16
<212> TYPE: DNA
<213> ORGANISM: Artificial Sequence
<220> FEATURE:
<223> OTHER INFORMATION: synthetic primer
```

```
-continued

<400> SEQUENCE: 20
gagggctgca gtcatt                                                          16
```